United States Patent [19]

Norris et al.

[11] Patent Number: 5,373,090
[45] Date of Patent: Dec. 13, 1994

[54] APROTININ ANALOGUES AND A PROCESS FOR THE PRODUCTION THEREOF

[75] Inventors: Kjeld Norris, Hellerup; Lars C. Petersen, Horsholm, both of Denmark

[73] Assignee: Novo Nordisk A/S, Bagsvaerd, Denmark

[21] Appl. No.: 598,737

[22] PCT Filed: Apr. 25, 1989

[86] PCT No.: PCT/DK89/00096
§ 371 Date: Nov. 19, 1990
§ 102(e) Date: Nov. 19, 1990

[87] PCT Pub. No.: WO89/10374
PCT Pub. Date: Nov. 2, 1989

[30] Foreign Application Priority Data

Apr. 26, 1988 [DK] Denmark .............................. 2254/88

[51] Int. Cl.$^5$ .......................... C07K 7/10; C12N 15/00
[52] U.S. Cl. .................................. 530/324; 435/69.2; 435/172.1
[58] Field of Search ................. 435/69.2, 172.1, 255; 530/324

[56] References Cited

U.S. PATENT DOCUMENTS 4,595,674  6/1986  Tschesche et al. .................... 514/9
5,118,668  6/1992  Auerswald et al. .................. 514/12

FOREIGN PATENT DOCUMENTS 0297362  1/1989  European Pat. Off. .
2188322  9/1987  United Kingdom .
2188933 10/1987  United Kingdom .

OTHER PUBLICATIONS

Schnabel et al., Biol. Chem. Hoppe-Seyler, vol. 367, pp. 1167–1176 (1986).
Fiovett: et al. "Primary Structure and Antiproteolytic Activity of a Kunits-type Inhibitor from Bovine Spleam." JBC, 260 (21) 11451–11455. 1985.

Primary Examiner—Garnette D. Draper
Assistant Examiner—Sally P. Teng
Attorney, Agent, or Firm—Steve T. Zelson; Cheryl H. Agris

[57] ABSTRACT

This invention relates to novel aprotinin analogues having a selected inhibition profile against serine proteases.

6 Claims, 5 Drawing Sheets

```
            3          5                  10                 15
         AspPheCysLeuGluProProTyrThrGlyProCysLysAlaArgIle
         AAAGAGATTTCTGTTTGGAACCTCCATACACTGGTCCATGTAAAGCTAGAATC
             CTAAAGACAAACCTTGGAGGTATGTGACCAGGTACATTTCGATCTTAG
                              PflMI 20                 25                 30                 35
         IleArgTyrPheTyrAsnAlaLysAlaGlyLeuCysGlnThrPheValTyrGly
         ATCAGATACTTCTACAACGCCAAGGCTGGTTTGTGTCAAACTTTCGTTTACGGT
         TAGTCTATGAAGATGTTGCGGTTCCGACCAAACACAGTTTGAAAGCAAATGCCA
                              StyI 40                 45                 50
         GlyCysArgAlaLysSerAsnAsnPheLysSerAlaGluAspCysMetArgThr
         GGCTGCAGAGCTAAGTCCAACAACTTCAAGTCTGCTGAAGACTGCATGAGAACT
         CCGACGTCTCGATTCAGGTTGTTGAAGTTCAGACGACTTCTGACGTACTCTTGA
             PstI 55        58
         CysGlyGlyAlaStop   (SEQ ID NO:33)
         TGTGGTGGTGCCTAAT   (SEQ ID NO:32)
         ACACCACCACGGATTAGATC   (SEQ ID NO:34)
                          XbaI
```

*FIG.1*

APROTININ ANALOGUES AND A PROCESS FOR THE PRODUCTION THEREOF

FIELD OF THE INVENTION

The present invention relates to novel aprotinin analogues and to a process for their production.

BACKGROUND OF THE INVENTION

Throughout the present specification the term naturally occuring amino acid (or amino acid residue) refers to one of the α-amino acids which are listed below together with the symbols used to designate the individual amino acid residues:

| Asp | Aspartic acid | Ile | Isoleucine |
|-----|---------------|-----|------------|
| Thr | Threonine | Leu | Leucine |
| Ser | Serine | Tyr | Tyrosine |
| Glu | Glutamine acid | Phe | Phenylalanine |
| Pro | Proline | His | Histidine |
| Gly | Glycine | Lys | Lysine |
| Ala | Alanine | Arg | Arginine |
| Cys | Cysteine | Trp | Tryptophane |
| Val | Valine | Gln | Glutamine |
| Met | Methionine | Asn | Asparagine |

All amino acids (or amino acid residues) mentioned in the present specification have the L-configuration, except glycine which has no chiral center.

Aprotinin (bovine pancreatic trypsin inhibitor, BPTI) is a polypeptide present in several bovine organs and tissues, such as lymph nodes, pancreas, lung, parotid gland, spleen and liver. It is a single chain polypeptide consisting of 58 amino acid residues cross-linked by three disulphide bridges in the following sequence:

Arg—Pro—Asp—Phe—Cys—Leu—Glu—Pro—Pro—Tyr—Thr—Gly—Pro—Cys—
1    2    3    4    5    6    7    8    9    10   11   12   13   14

Lys—Ala—Arg—Ile—Ile—Arg—Tyr—Phe—Tyr—Asn—Ala—Lys—Ala—Gly—
15   16   17   18   19   20   21   22   23   24   25   26   27   28

Leu—Cys—Gln—Thr—Phe—Val—Tyr—Gly—Gly—Cys—Arg—Ala—Lys—Arg—
29   30   31   32   33   34   35   36   37   38   39   40   41   42

Asn—Asn—Phe—Lys—Ser—Ala—Glu—Asp—Cys—Met—Arg—Thr—Cys—Gly—
43   44   45   46   47   48   49   50   51   52   53   54   55   56

Gly—Ala    (SEQ ID NO:1)
57   58

The three disulphide bridges are situated between Cys(5)-Cys(55), Cys(14)-Cys(38) and Cys(30)-Cys(51), respectively.

Aprotinin inhibits various serine proteases, such as trypsin, chymotrypsin, plasmin and kallikrein and is used for the treatment of acute pancreatitis, various states of shock syndroms, hyperfibrinolytic haemorrhage, and myocardial infarction. Administration of aprotinin in high doses significantly reduces blood loss in connection with cardiac surgery.

Aprotinin is extracted from various bovine organs or tissues, such as lung, pancreas and parotid glands. Extraction from animal tissues is a cumbersome process and requires large amounts of the bovine organ or tissue. Aprotinin may also be produced by recombinant DNA-technology by insertion of a gene coding for aprotinin in a suitable microorganism which when cultured in a suitable nutrient medium produces the desired product.

Production of aprotinin analogues in *E. coli* is described in EP published patent application No. 238,993 and production of aprotinin in yeast is described in Danish patent application No. 4501/87.

Certain aprotinin analogues and derivatives have been described, see for instance Jering H. and Tschesche H., Eur.J.Biochem. 61 (1976), 453–463 describing replacement of Lys(15) with Arg, Phe or Trp or U.S. Pat. No. 4,595,674 describing aprotinin analogues in which the lysine residue in position 15 in the active center of the aprotinin has been replaced by Gly, Ala, Val, Leu, Ile, Met, Arg, L-α-amino butyric acid, L-norvaline, L-norleucine, dehydroalanine or L-homoserine. Also, the above mentioned EP No. 238,993 describes aprotinin analogues having Lys(15) substituted by Arg, Val, Ile, Leu, Phe, Gly, Ser, Trp, Tyr or Ala and/or Met(52) substituted by Glu, Leu, Val, Thr or Ser.

The known aprotinin analogues are claimed to have modified effects and efficacies towards different proteinases. For instance aprotinin(15 Val) has a relatively high selectivity for granulocyte elastase and an inhibition effect on collagenase, aprotinin(15Ala) has only a weak inhibitory effect on elastase and aprotinin(15Gly) has an outstanding antitrypsin activity and surprisingly inhibits kallikrein.

SUMMARY OF THE INVENTION

It is the purpose of the present invention to provide novel aprotinin analogues having a more specific inhibitory effect towards certain serine proteases, such as elastase, kallikrein, t-PA, urokinase and coagulation factors, such as thrombin.

The present invention is based on the surprising fact that replacement of Arg in position 17 of aprotinin(3-58;42Ser) with Ala or of Arg in position 17 with Ala and of Ile in position 19 of aprotinin (3-58;42Ser) with Glu gives rise to a substantial increase in the inhibition of human plasma kallikrein. This is even more pronounced on replacement of Lys in position 15 with Arg and of Arg in position 17 with Ala in aprotinin (3-58; 42Ser).

Accordingly, the present invention is related to aprotinin analogues in which at least one of the amino acid residues 16 to 19 have been replaced by another naturally occuring amino acid residue.

In the above mentioned Danish patent application No. 4501/87 aprotinin analogues with certain amino acid residue substitutions and/or deletions are described. The aim of these amino acid residue substitutions and/or deletions is to avoid proteolytical cleavage at certain basic amino acid residues during the production of the aprotinin analogue in yeast. In particular amino acid residues 1 and 2 may be deleted and one of the basic amino acid residues at the dibasic sequence 41-42 may be replaced by another amino acid residue. It has been shown that such aprotinin analogues are produced in high yields in yeast and exhibit the same characteristics as native aprotinin.

To ensure high production in yeast the present aprotinin analogues may further be modified in a similar way. Accordingly the present aprotinin analogues besides being modified in the sequence from amino acid 16 to 19 may also be modified at sequence 1-2 and 41-42, respectively provided that such further modification does not have an adverse effect on the goal of the present invention.

The present aprotinin analogues may furthermore be modified in position 15 by insertion at this position of another naturally occuring amino acid residue including the known substitutions with naturally occuring amino acid residues.

Native aprotinin contains a disulphide bridge between Cys(14) and Cys(38) which is strongly involved in the tertiary structuring around the active site at Lys (15). This disulphide bond may be split by reducing agents. A more convenient way to avoid having a disulphide bridge at this position in the molecule would be to substitute the cysteine residues with other residues or simply to delete these residues. Accordingly, the present aprotinin analogues may furthermore be modified so that they do not contain a disulphide bridge between Cys(14) and Cys(38). This might impart further interesting characteristics to the molecule.

Finally modifications at positions 12 and 13 might be considered.

Accordingly in its broadest aspect the present invention relates to aprotinin analogues being modified in the sequence from amino acid residue 12 to 19 provided that if Lys(15) has been replaced by another amino acid then at least one further amino acid residue in said sequence has been substituted or deleted. The present aprotinin analogues may furthermore as described above be modified in the known way at the sequences 1-2 and 41-42.

According to a further aspect of the present invention there is provided a method for producing the above aprotinin analogues by cultivation of a yeast strain containing a replicable expression vector containing a gene encoding the aprotinin analogues in a suitable nutrient medium followed by recovery of the desired product from the culture medium.

BRIEF DESCRIPTION OF THE DRAWINGS

The present invention will be further illustrated by reference to the accompanying drawings in which:

FIG. 1 shows a synthetic gene encoding aprotinin (3-58; 42Ser);

DETAILED DESCRIPTION OF THE PRESENTLY PREFERRED EMBODIMENTS

Figure 2:
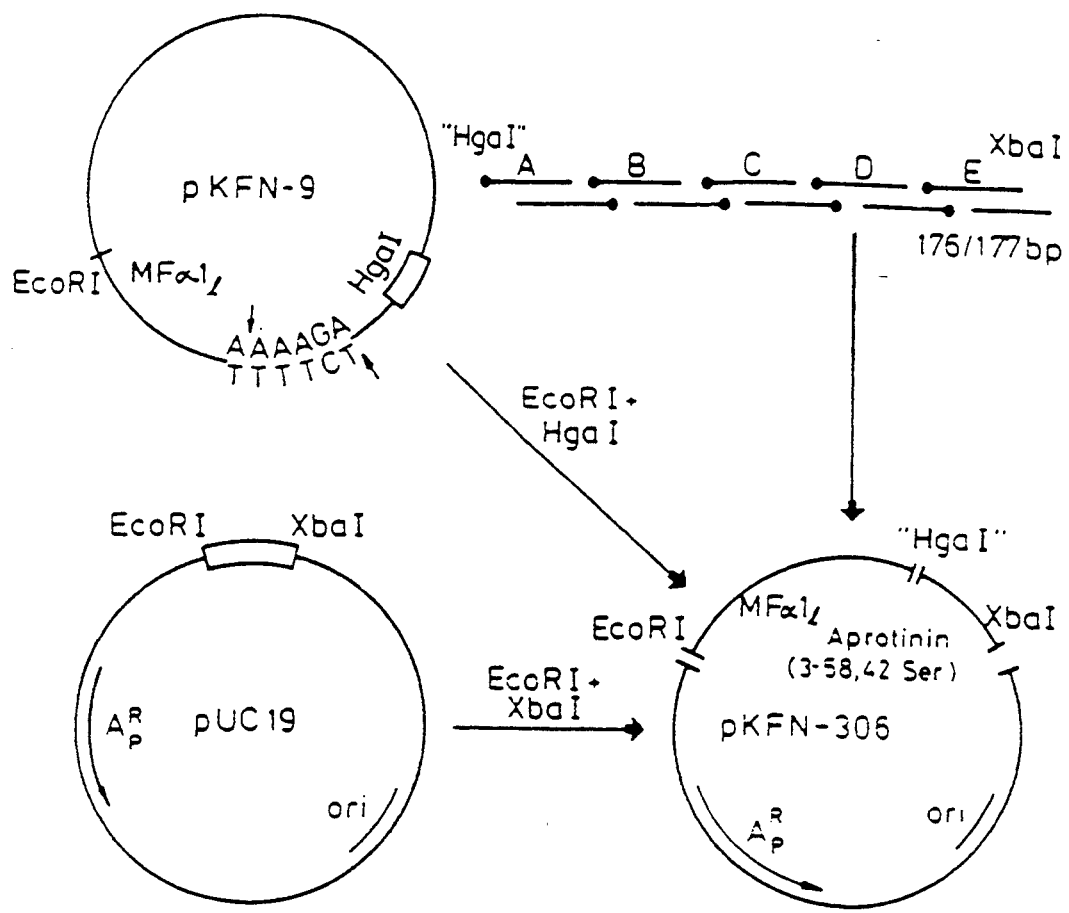
FIG. 2 illustrates the construction of the plasmid pKFN 306.

The present aprotinin analogues may be represented by the following formula (I):

$X_1$—Asp—Phe—Cys—Leu—Glu—Pro—Pro—Tyr—Thr—$X_2$—$X_3$—$X_4$—$X_5$—$X_6$—$X_7$— (I)

$X_8$—$X_9$—Arg—Tyr—Phe—Tyr—Asn—Ala—Lys—Ala—Gly—Leu—Cys—Gln—Thr—

Phe—Val—Tyr—Gly—Gly—$X_{10}$—Arg—Ala—$X_{11}$—$X_{12}$—Asn—Asn—Phe—Lys—

Ser—Ala—Glu—Asp—Cys—Met—Arg—Thr—Cys—Gly—Gly—Ala (SEQ ID NO:2)

in which $X_1$ is Arg-Pro, Pro or hydrogen, preferably Arg-Pro or hydrogen, most preferred hydrogen; $X_2$ is any naturally occuring amino acid residue, preferably Gly; $X_3$ is any naturally accuring amino acid residue, preferably Pro; $X_4$ and $X_{10}$ are each any naturally ocurring amino acid residue, preferably they are both Cys or both Ala, most preferred they are both Cys; $X_5$ is Lys, Arg, Val, Thr, Ile, Leu, Phe, Gly, Ser, Met, Trp, Tyr or Ala, preferably Lys or Arg, with the proviso that when $X_5$ is different from Lys, then at least one of $X_2$ to $X_4$ and $X_6$ to $X_9$ are different from the amino acid residue at the corresponding position in native aprotinin; $X_6$ is Ala or Gly, preferably Ala; $X_7$ is any naturally occuring amino acid residue, preferably Ala or Gly; $X_8$ is Ile, Leu, Met, Val or Phe, preferably Ile; $X_9$ is any naturally occuring amino acid residue, preferably Ile or Glu; $X_{11}$ is any naturally Occuring amino acid residue, preferably Lys or Arg; $X_{12}$ is Lys, Arg or Ser at least one of the amino acid residues $X_2$ to $X_9$, preferably $X_5$ to $X_9$, more preferred $X_6$ to $X_9$ being different from the corresponding amino acid residue in native aprotinin.

According to a more narrow aspect the present aprotinin analogues may be represented by the following formula (II):

$X_1$—Asp—Phe—Cys—Leu—Glu—Pro—Pro—Tyr—Thr—Gly—Pro—Cys—$X_5$—$X_6$— (II)

$X_7$—$X_8$—$X_9$—Arg—Tyr—Phe—Tyr—Asn—Ala—Lys—Ala—Gly—Leu—Cys—Gln—

Thr—Phe—Val—Tyr—Gly—Gly—Cys—Arg—Ala—$X_{11}$—$X_{12}$—Asn—Asn—Phe—

Lys—Ser—Ala—Glu—Asp—Cys—Met—Arg—Thr—Cys—Gly—Gly—Ala (SEQ ID NO:3)

in which $X_1$, $X_5$, $X_6$, $X_7$, $X_8$, $X_9$, $X_{11}$ and $X_{12}$ are as defined above for formula (I), at least one of the amino acid residues $X_5$ to $X_9$, preferably $X_6$ to $X_9$ being different from the corresponding amino acid residue in native aprotinin.

According to an even narrower aspect the aprotinin analogues may be represented by the following formula (III):

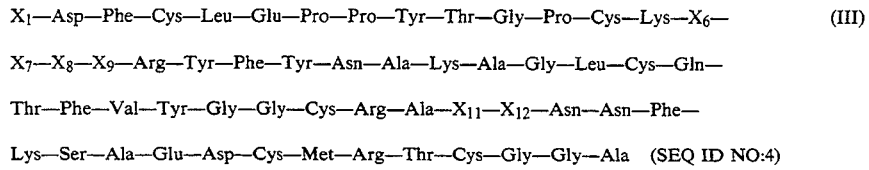

X₁—Asp—Phe—Cys—Leu—Glu—Pro—Pro—Tyr—Thr—Gly—Pro—Cys—Lys—X₆— (III)

X₇—X₈—X₉—Arg—Tyr—Phe—Tyr—Asn—Ala—Lys—Ala—Gly—Leu—Cys—Gln—

Thr—Phe—Val—Tyr—Gly—Gly—Cys—Arg—Ala—X₁₁—X₁₂—Asn—Asn—Phe—

Lys—Ser—Ala—Glu—Asp—Cys—Met—Arg—Thr—Cys—Gly—Gly—Ala (SEQ ID NO:4)

in which $X_1$, $X_6$, $X_7$, $X_8$, $X_9$, $X_{11}$ and $X_{12}$ are as defined above for formula (I), at least one of the amino acid residues $X_6$ to $X_9$ being different from the corresponding amino acid residue in native aprotinin.

Examples of preferred aprotinin analogues according to the present invention are aprotinin(3-58; 17Ala+42Ser), which lacks the first two amino acid residues of native aprotinin and has Ala substituted for Arg in position 17 and Ser substituted for Arg in position 42; aprotinin (3-58; 17Ala+19Glu+42Ser), which lacks the first two amino acid residues of native aprotinin and has Ala substituted for Arg in position 17, Glu substituted for Ile in position 19 and Ser substituted for Arg in position 42; and aprotinin (3-58; 15Arg+17Ala+42Ser) which lacks the first two amino acid residues of native aprotinin and has Arg substituted for Lys in position 15, Ala substituted for Arg in position 17 and Ser substituted for Arg in position 42, respectively.

Further examples of aprotinin analogues according to the present invention are:
Aprotinin(3-58; 17Ala)
Aprotinin(3-58; 17Ala+19Glu)
Aprotinin(3-58; 15Arg+17Ala)
Aprotinin(17Ala+42Ser)
Aprotinin(15Arg+17Ala+42Ser)
Aprotinin(17Ala)
Aprotinin(17Ala+19Glu)
Aprotinin(15Arg+17Ala)

For secretion purposes the DNA-sequence encoding the desired aprotinin-analogue is fused to a DNA-sequence encoding a signal and leader peptide sequence. The signal and leader peptides are cleaved off by the transformed microorganism during the secretion of the expressed protein product from the cells ensuring a more simple isolation procedure of the desired product. A well suited leader peptide system for yeast is the yeast MFα1 leader sequence of a part thereof (Kurjan, J. and Herskowitz, I., Cell 30 (1982) 933-943). However, any signal- or leader-sequence which provides for secretion in yeast may be employed and the present invention is not contemplated to be restricted to a specific secretion system.

For expression purposes a promoter sequence is positioned upstream to the DNA-sequence for the desired protein product. Preferably a promoter from a gene indigenous to the yeast host organism is used, e.g. the promoter of the TPI-(triose phosphate isomerase) gene. The DNA-sequence for the desired product will be followed by a transcription terminator sequence, preferably a terminator sequence from a gene indigenous to the host yeast organism, e.g. the terminator of the TPI-gene or the MFα1 gene.

The DNA-sequence encoding the desired aprotinin analogue fused to appropriate promoter, signal, leader and terminator sequences is inserted into an expression vector for expression of the aprotinin analogue in yeast.

The expression vector may be a plasmid capable of independent replication in yeast or capable of integration into the yeast chromosome. The plasmid may preferably be stabilized against plasmid loss by the host microorganism by incorporation of a gene essential for the viability or normal growth of the host cells, e.g. a gene coding for cell division, cell wall biosynthesis, protein synthesis, etc.

EXAMPLE 1

Aprotinin(3-58; 17Ala+42Ser) (KFN 396)

A sequence encoding aprotinin(3-58; 42Ser) was constructed from a number of oligonucleotides by ligation.

The oligonucleotides were synthesized on an automatic DNA synthesizer using phosphoramidite chemistry on a controlled pore glass support (S. L. Beaucage and M. H. Caruthers (1981) Tetrahedron Letters 22, 1859–1869).

The following 10 oligonucleotides were synthesized:

| | | | |
|---|---|---|---|
| I: | AAAGAGATTTCTGTTTGGAACCTCCATACACTGGTCC  37-mer | (SEQ ID NO:5) | Duplex A |
| II: | TTACATGGACCAGTGTATGGAGGTTCCAAACAGAAACT  38-mer | (SEQ ID NO:6) | |
| III: | ATGTAAAGCTAGAATCATCAGATACTTCTACAACG  35-mer | (SEQ ID NO:7) | Duplex B |
| IV: | CTTGGCGTTGTAGAAGTATCTGATGATTCTAGCT  34-mer | (SEQ ID NO:8) | |
| V: | CCAAGGCTGGTTTGTGTCAAACTTTCGTTTACGGTGGCT  39-mer | (SEQ ID NO:9) | Duplex C |
| VI: | CTCTGCAGCCACCGTAAACGAAAGTTTGACACAAACCAGC  40-mer | (SEQ ID NO:10) | |

-continued

VII: GCAGAGCTAAGTCCAACAACTTCAAGT (SEQ ID NO:11) ⎫
    27-mer                                       ⎬ Duplex D VIII: AGCAGACTTGAAGTTGTTGGACTTAG (SEQ ID NO:12) ⎭
    26-mer IX: CTGCTGAAGACTGCATGAGAACTTGTGGTGGTGCCTAAT (SEQ ID NO:13) ⎫
    39-mer                              ⎬ Duplex E X: CTAGATTAGGCACCACCACAAGTTCTCATGCAGTCTTC (SEQ ID NO:14) ⎭
   38-mer 5 duplexes A-E were formed from the above 10 oligonucleotides as shown in FIG. 1 and 2.

20 pmole of each of the duplexes A-E was formed from the corresponding pairs of 5'-phosphorylated oligonucleotides I-X by heating for 5 min. at 90° C. followed by cooling to room temperature over a period of 75 minutes. The five duplexes were mixed and treated with T4 ligase. The synthetic sequence was isolated as a 176 bp band after electrophoresis of the ligation mixture on a 2% agarose gel.

The synthetic sequence was ligated to a 330 bp EcoRI-HgaI fragment from plasmid pKFN9 coding for MFαl signal and leader sequence(l-85) and to the large EcoRI-XbaI fragment from pUC19. The construction of pKFN9 containing a HgaI site immediately after the MFαl leader sequence is described in European patent application No. 0214826.

The ligation mixture was used to transform a competent E. coli strain (r−, m30) selecting for ampicillin resistance. Sequencing of a 32p-XbaI-EcoRI fragment (Maxam, A. and Gilbert, W. (1980) Methods Enzymol. 65, 499-560) showed that plasmids from the resulting colonies contained the correct DNA-sequence for aprotinin(3-58; 42Ser).

One plasmid pKFN306 was selected for further use. The construction of plasmid pKFN306 is illustrated in FIG. 2.

Figure 3:
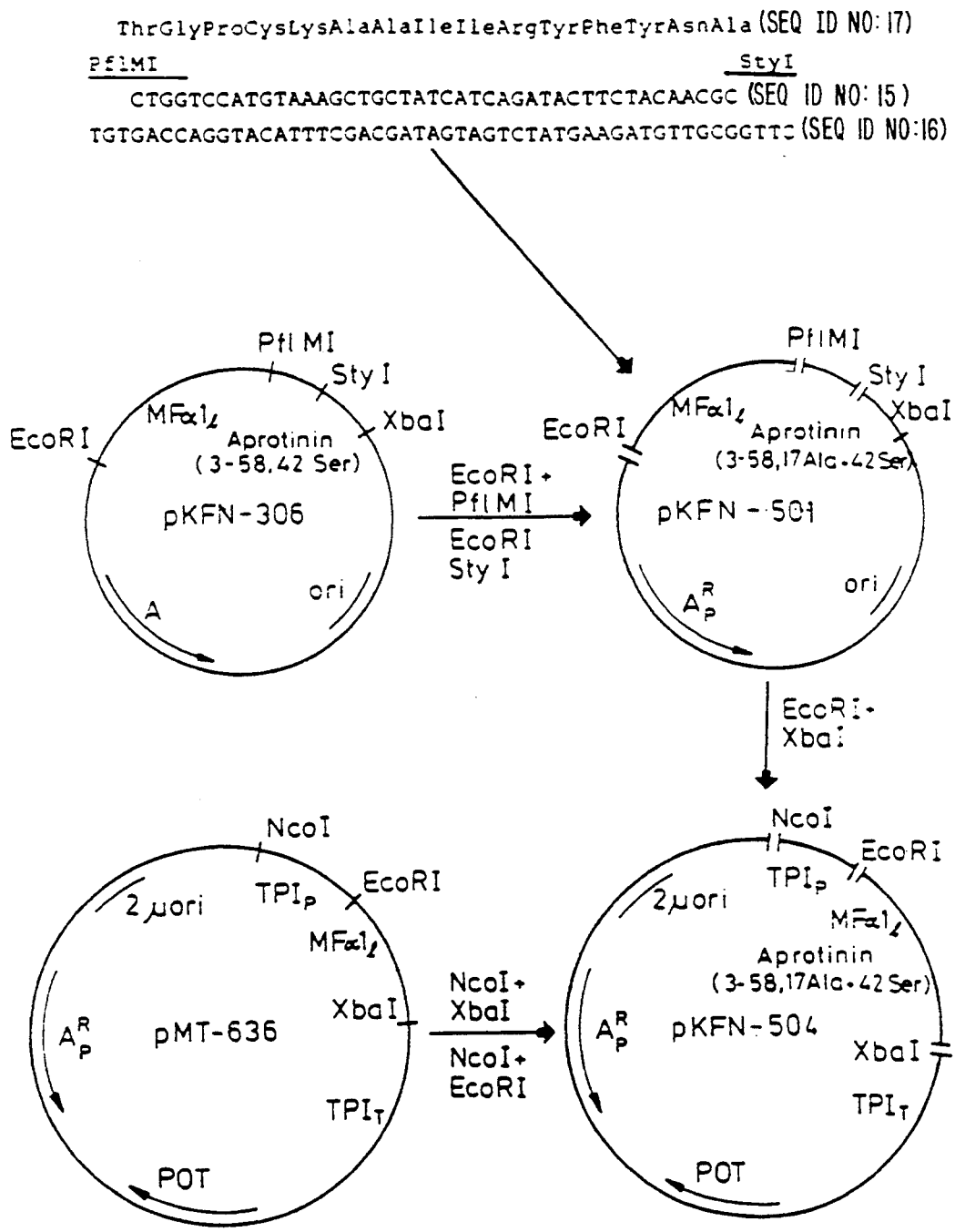
FIG. 3 illustrates the construction of the plasmid pKFN 504.
Figure 4:
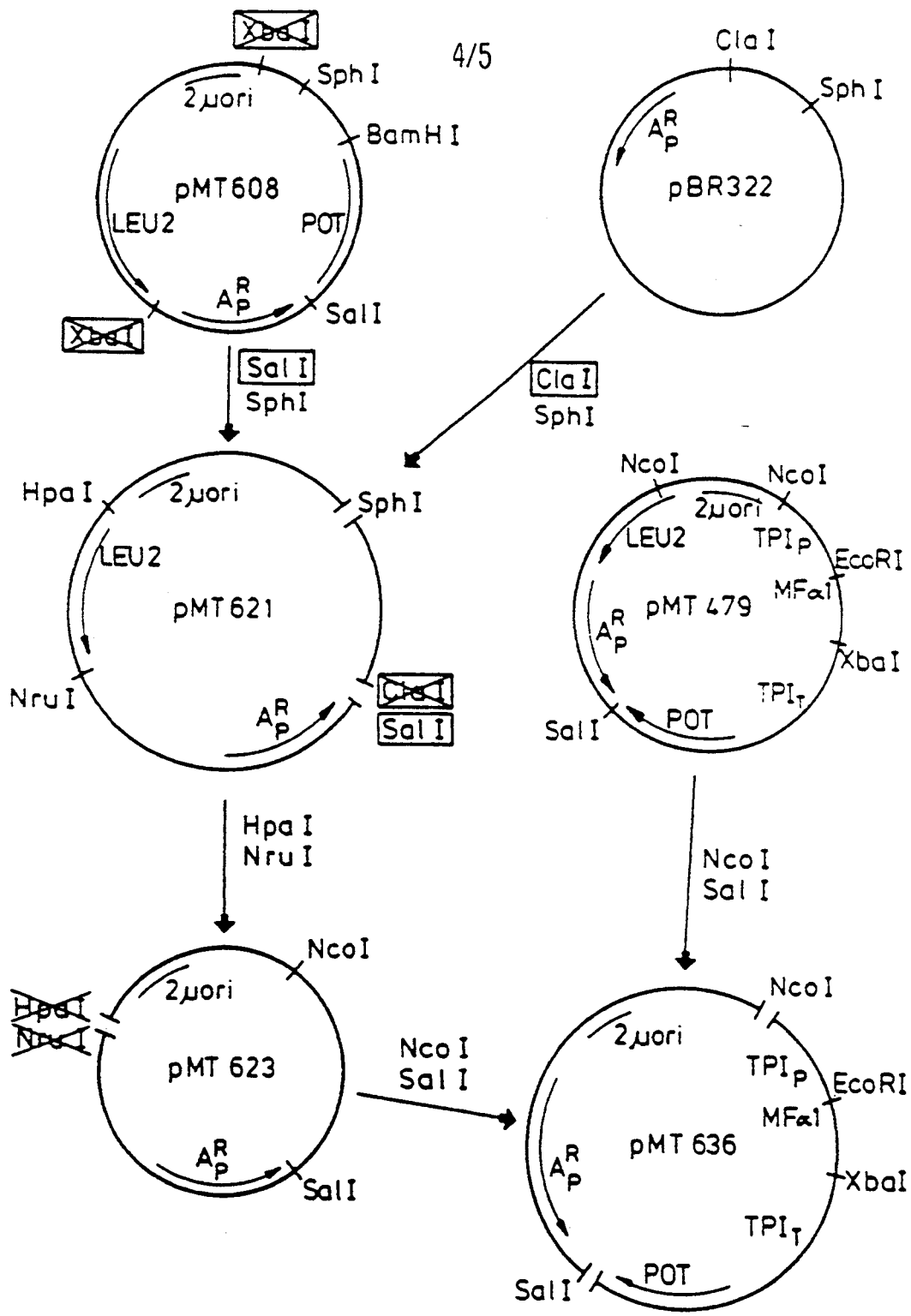
FIG. 4 illustrates the construction of the plasmid pMT 636.

To introduce Ala in position 17 the following oligonucleotides were synthesized as described above:

pKFN501 was cut with EcoRI and XbaI and the 0.5 kb fragment was ligated to the 9.5 kb NcoI-XbaI fragment from pMT636 and the 1.4 kb NcoI-EcoRI fragment from pMT636, resulting in plasmid pKFN504, see FIG. 3. Plasmid pMT636 was constructed from pMT608 after deletion of the LEU-2 gene and from pMT479, see FIG. 4. pMT608 is described in European patent application No. 195691. pMT479 is described in European patent application No. 163529. pMT479 contains the Schizo. pombe TPI gene (POT), the S. cerevisiae triosephosphate isomerase promoter and terminator, TPI$_P$ and TPI$_T$ (Alber, T. and Kawasaki, G. (1982) J.Mol.Appl.Gen. 1, 419–434). Plasmid pKFN504 contains the following sequence:

TPI$_P$-MFαl-signal-leader(1-85)-aprotinin(3-58;17Ala+42Ser)-TPI$_T$ where MFαl is the S. cerevisiae mating factor alpha 1 coding sequence (Kurjan, J. and Herskowitz, I. (1982) Cell 30, 933–943), signal-leader(1-85) means that the sequence contains the first 85 amino acid residues of the MFαl signal-leader sequence and aprotinin(3-58; 17Ala+42Ser) is the synthetic sequence encoding an aprotinin derivative lacking the first two amino acid residues at the N-terminus and having amino acid residues 17 and 42 replaced by an Ala and a Ser residue, respectively.

S. cerevisiae strain MT663 (E2-7B XE11-36 a/α, ΔtpiΔtpi, pep 4-3/pep 4-3) was grown on YPGaL (1% Bacto yeast extract, 2% Bacto peptone, 2% galactose, Ia: CTGGTCCATGTAAAGCTGCTATCATCAGATACTTCTACAACGC (SEQ ID NO:15)
   43-mer IIa: CTTGGCGTTGTAGAAGTATCTGATGATAGCAGCTTTACATGGACCAGTGT (SEQ ID NO:17)
   50-mer The oligonucleotides were 5'-O-phosphorylated by treatment with ATP and T4-kinase.

A duplex formed by annealing 5'-phosphorylated oligonucleotides Ia and IIa was ligated to the 352 bp EcoRI-PflMI fragment and the 3 kbp EcoRI-StyI fragment, both from pKFN306. pKFN306 encodes the S.cerevisiae mating factor αl signal-leader (1-85) fused to the synthetic aprotinin (3-58; 42Ser) gene.

The ligation mixture was used to transform a competent E. coli strain (r−, m+) selecting for ampicillin resistance. Sequencing of a 32P-XbaI-EcoRI fragment (Maxam, A. and Gilbert, W. (1980) Methods Enzymol. 65, 499-560) showed that plasmids from the resulting colonies contained the correct DNA-sequence for aprotinin(3-58; 17Ala+42Ser).

One plasmid, pKFN501 was selected for further use. The construction of plasmid pKFN501 is illustrated in FIG. 3.

1% lactate) to an optical density at 600 nm of 0.6.

100 ml of culture was harvested by centrifugation, washed with 10 ml of water, recentrifuged and resuspended in 10 ml of (1.2M sorbitol, 25 mM Na$_2$EDTA pH=8.0, 6.7 mg/ml dithiotreitol). The suspension was incubated at 30° C. for 15 minutes, centrifuged and the cells resuspended in 10 ml of (1.2M sorbitol, 10 mM Na$_2$EDTA, 0.1M sodium citrate pH=5.8, 2 mg Novozym ®️ 234). The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCl (Tris=-Tris(hydroxymethyl)-aminomethan) pH=7.5) and resuspended in 2 ml of CAS. For transformation 0.1 ml of CAS-resuspended cells were mixed with approximately 1 μg of plasmid pKFN504 and left at room temperature for 15 minutes. 1 ml of (20% polyethylenglycol 4000, 10 mM CaCl$_2$, 10 mM Tris HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl₂, 14 μg/ml leucine) and incubated at 30° C. for 2 hours. The suspension was then centrifuged and the pellet resuspended in 0.5 ml of 1.2M sorbitol. 6 ml of top agar (the SC medium of Sherman et al. , (Methods in Yeast Genetics, Cold Spring Harbor Laboratory, 1981) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN396 was chosen for further characterization.

Yeast strain KFN396 was grown on YPD medium (1% yeast extract, 2% peptone (from Difco Laboratories), and 2% glucose). A 1 liter culture of the strain was shaken at 30° C. to an optical density of 600 nm of 13. After centrifugation the supernatant was purified by FPLC ion exchange chromatography. The yeast supernatant was filtered through a 0.22 μm Millex ® GV filter unit and 1 ml was applied on a MonoS cation exchange column (0.5×5 cm) equilibrated with 20 mM Bicine, pH 8.7. After wash with equilibration buffer the column was eluated with a linear NaCl gradient (0–1M) in equilibration buffer. Trypsin inhibitor activity was quantified in the eluated fractions by spectrophotometric assay and furthermore by integration $$E_{280}^{1\%} \text{ (aprotinin)} = 8.3$$

The yield was about 4.3 mg/liter of aprotinin(3-58; 17Ala+42Ser).

For amino acid analysis the yeast supernatant (7 ml) was adjusted to pH 8.7 with 0.1M NaOH and filtered (0.22 μm). The effluent from a Q-Sepharose anion exchange column (1×4 cm) equilibrated with 20 mM Bicine, pH 8.7 was applied to a MonoS cation exchange column (0.5×5 cm). The cation exchange chromatography was carried out as described above. Concentration of the gradient eluated aprotinin (3-58) was made by rechromatography on MonoS and elution with steep NaCl-gradient. The collected fractions were further concentrated by vacuum centrifugation to about 100 μl and applied to a RP-HPLC column (Vydac C4, 4.6×250 mm). Eluation was carried out with CH₃CN gradient in 0.1% TFA. The collected fractions were concentrated to about 100 μl by vacuum centrifugation and samples were taken for amino acid analysis.

The amino acid analysis appears from the following Table 1. From this table it appears that the product has the expected amino acid composition.

TABLE 1

| Amino acid | Theoretical | Aprotinin (3-58;17 Ala + 42 Ser) (found) |
|---|---|---|
| Asx | 5 | 4.90 |
| Thr | 3 | 2.95 |
| Ser | 2 | 2.10 |

TABLE 1-continued

| Amino acid | Theoretical | Aprotinin (3-58;17 Ala + 42 Ser) (found) |
|---|---|---|
| Glx | 3 | 3.01 |
| Pro | 3 | 3.14 |
| Gly | 6 | 5.93 |
| Ala | 7 | 6.69 |
| Cys | 6 | 5.91 |
| Val | 1 | 1.02 |
| Met | 1 | 0.99 |
| Ile | 2 | 2.00 |
| Leu | 2 | 1.98 |
| Tyr | 4 | 3.73 |
| Phe | 4 | 3.75 |
| Lys | 4 | 4.29 |
| Arg | 3 | 3.21 |
| Total | 56 | 55.60 |

EXAMPLE 2

Aprotinin(3-58;17Ala+19Glu+42Ser) (KFN399)

A synthetic gene encoding aprotinin(3-58; 17Ala+19Glu+42Ser) was constructed as described in Example 1. The following oligonucleotides Ib and IIb were used instead of Ia and IIa:

Ib: CT GGT CCA TGT AAA GCT GCT ATC GAA AGA TAC TTC TAC AAC GC (SEQ ID NO:18)
43-mer IIb: CTT GGC GTT GTA GAA GTA TCT TTC GAT AGC AGC TTT ACA TGG ACC AGT GT (SEQ ID NO:19)
50-mer The pUC19 derived plasmid pKFN503 was constructed in a similar way as pKFN501.

By following the Procedure of Example 1 a plasmid pKFN507 was obtained containing the following construction TPI<sub>P</sub>-MFα1-signal-leader
(1-85)-aprotinin(3-58;17Ala+19Glu
+42Ser)-TPI<sub>T</sub> where aprotinin(3-58; 17Ala+19Glu+42Ser) is the synthetic gene encoding an aprotinin derivative lacking the first two amino acid residues at the N-terminal and having the residues 17, 19 and 42 of native aprotinin replaced by an alanine, a glutamic acid and a serine residue respectively.

Plasmid pKFN507 was transformed in yeast strain MT663 as described above and culturing of the transformed strain KFN399 gave about 10 mg/liter of aprotinin(3-58; 17Ala+19Glu+42Ser).

The amino acid analysis appears from the following Table 2 and confirms the expected amino acid composition.

TABLE 2

| Amino acid | Theoretical | Aprotinin (3-58;17 Ala + 19 Glu + 42 Ser) (found) |
|---|---|---|
| Asx | 5 | 4.96 |
| Thr | 3 | 2.83 |
| Ser | 2 | 1.90 |
| Glx | 4 | 4.08 |
| Pro | 3 | 2.98 |
| Gly | 6 | 5.98 |
| Ala | 7 | 6.92 |
| Cys | 6 | 5.06 |
| Val | 1 | 0.99 |
| Met | 1 | 0.86 |
| Ile | 1 | 0.99 |

TABLE 2-continued

| Amino acid | Theoretical | Aprotinin (3-58;17 Ala + 19 Glu + 42 Ser) (found) |
|---|---|---|
| Leu | 2 | 1.99 |
| Tyr | 4 | 3.77 |
| Phe | 4 | 3.89 |
| Lys | 4 | 4.07 |
| Arg | 3 | 3.06 |
| Total | 56 | 54.36 |

EXAMPLE 3

Aprotinin(3-58;15Arg+17Ala+42Ser) (KFN773).

A synthetic gene encoding aprotinin(3-58; 15Arg+17Ala+42Ser) was constructed as described in Example 1. The following oligonucleotides Ic and IIc were used instead of Ia and IIa:

Ic: CT GGT CCA T GT AGA GCT GCT AT CAT CAG AT ACT T CT AC AAC GC (SEQ ID NO:20)
43-mer IIc: CT T GGC GT T GT AGA AGT AT CT GAT GAT AGC AGC T CT AC AT GGA CC AGT GT (SEQ ID NO:21)
50-mer The pUC19 derived plasmid pKFN777 was constructed in a similar way as pKFN501.

By following the procedure of Example 1 a plasmid pKFN807 was obtained containing the following construction TPI$_P$-MFα1-signal-leader(1-85)-aprotinin(3-58;15Arg+17Ala +42Ser)-TPI$_T$ where aprotinin(3-58; 15Arg+17Ala+42Ser) is the synthetic gene encoding an aprotinin derivative lacking the first two amino acid residues at the N-terminal and having the residues 15, 17 and 42 of native aprotinin replaced by an arginine, an alanine and a serine residue, respectively.

Plasmid pKFN807 was transformed in yeast strain MT663 as described above and culturing of the transformed strain KFN773 gave about 8.5 mg/liter of aprotinin(3-58; 15Arg+17Ala+42Ser).

The amino acid analysis is shown in Table 3 and confirms the expected amino acid composition.

TABLE 3

| Amino acid | Theoretical | Aprotinin (3-58;15 Arg + 17 Ala + 42 Ser) (found) |
|---|---|---|
| Asx | 5 | 4.95 |
| Thr | 3 | 2.85 |
| Ser | 2 | 1.81 |
| Glx | 3 | 3.01 |
| Pro | 3 | 3.05 |
| Gly | 6 | 5.92 |
| Ala | 7 | 6.91 |
| Cys | 6 | 5.31 |
| Val | 1 | 1.02 |
| Met | 1 | 0.73 |
| Ile | 2 | 1.41 |
| Leu | 2 | 1.99 |
| Tyr | 4 | 3.80 |
| Phe | 4 | 3.94 |
| Lys | 3 | 2.97 |
| Arg | 4 | 4.24 |
| Total | 56 | 53.91 |

The slightly lowered content of Ile compared with the theoretical value can most probably be ascribed to incomplete hydrolysis of Ile(18)-Ile(19). This is well known in the art.

EXAMPLE 4

Inhibition of Serine Proteases from Plasma by Aprotinin(3-58; 17Ala+42Ser) (KFN396) and Aprotinin(3-58; 17Ala+19Glu+42Ser) (KFN399), Aprotinin(3-58;15Arg+42Ser) (KFN772) and Aprotinin(3-58; 15Arg+17Ala+42Ser) (KFN773).

Aprotinin(3-58; 17Ala+42Ser) (KFN396), aprotinin(3-58; 17Ala+19Glu+42Ser) (KFN399) and aprotinin (3-58; 15Arg+17Ala+42Ser) (KFN773) were purified as described above. As native, bovine pancreatic aprotinin(1-58) batch B 5029-65 (67000 KIU/mg) from NOVO (Bagsvaerd, Denmark) was used. The concentration was calculated using $E_{280}$ nm=8.3 and $M_r$=6500. Human plasma kallikrein was obtained from Sigma (St. Louis, Mo.), bovine factor Xa was purified according to (H. Nobukazu et al. J.Biochem. 97 (1985)1347–1355), human factor IIa (thrombin) was a gift from Dr. W. Lawson (New York State Dept. of Health, Albany, N.Y.), recombinant human factor VIIa was from NOVO (Bagsvaerd, Denmark) and recombinant human protein Ca was from ZymoGenetics, Inc. (Seattle, Wash.). Substrate S 2302 (H-D-Pro-Phe-Arg-p-nitroanilide) substrate S2238 (H-D-Phe-Pip-Arg-p-nitroanilide) and substrate S2366 (Glu-Pro-Arg-p-nitroanilide) were from Kabi (Stockholm, Sweden). Substrate FXa-1 (methoxycarbonyl DCH-Gly-Arg-p-nitroanilide) was from NycoMed (Oslo, Norway). The experiments were performed in 100 mM NaCl, 50 mM Tris-HCl 0.01% Tween80, pH 7.4 at 25° C.

Figure 5A:
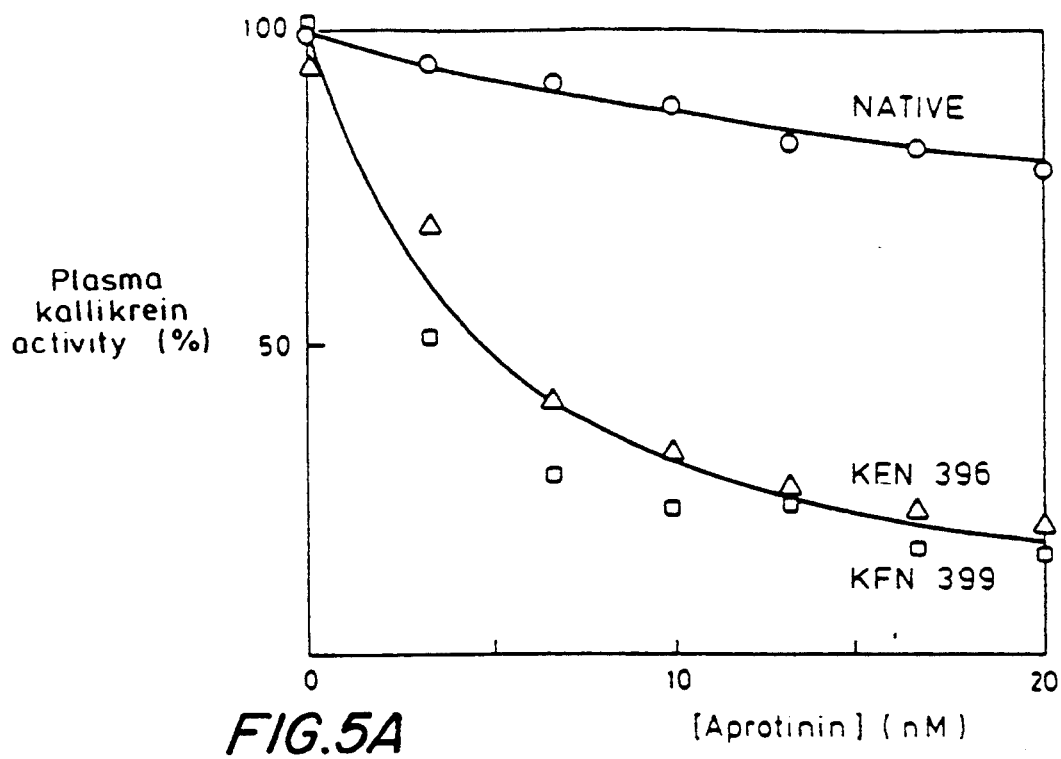
FIG. 5A illustrates the inhibition of plasma kallikrein by native aprotinin and by the aprotinin analogues KFN 396 and KFN 399.
Figure 5B:
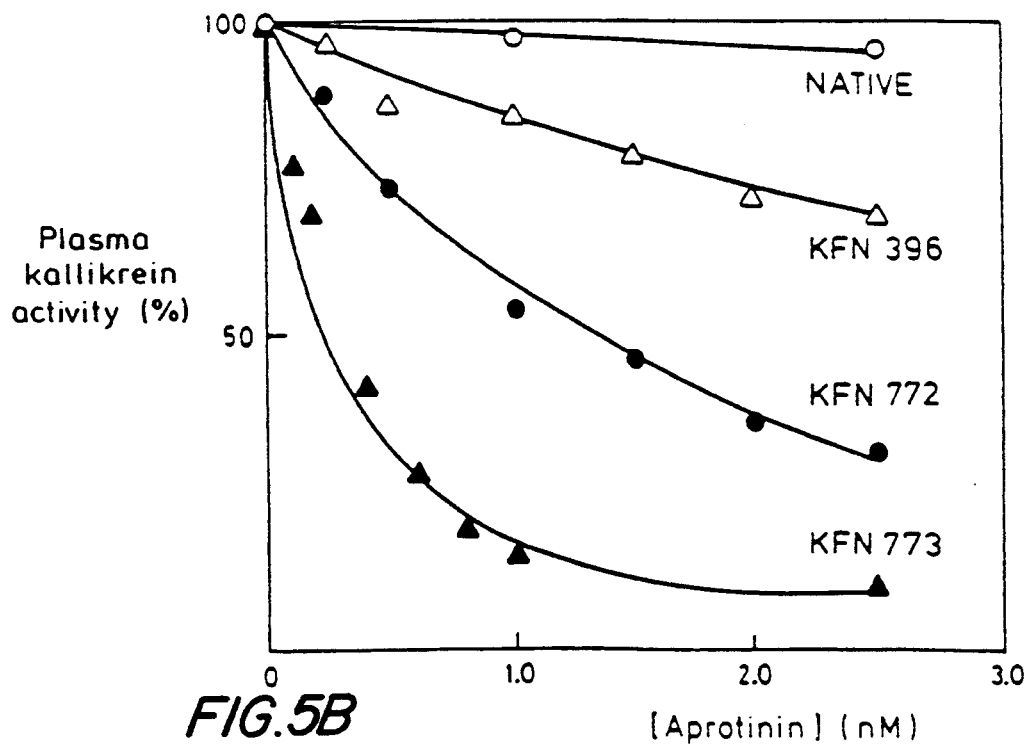
FIG. 5B illustrates the inhibition of plasma kallikrein by native aprotinin and by the aprotinin analogues KFN 396, KFN 772 and KFN 773.

Human plasma kallikrein (3 nM) was incubated with aprotinin (0–20 nM) for 30 minutes in a micro-titer well. Substrate S 2302 (0.6 mM) was added to a final volume of 300 μand the rate of nitroaniline generation was measured at 405 nm by means of a Micro ELISA ® Autoreader MR 580 from Dynatech Laboratories. The rate is proportional to the concentration of free enzyme. The inhibition of plasma kallikrein by native aprotinin and the four analogues KFN 396, KFN 399, KFN 772 and KFN 773 is shown in FIGS. 5A and 5B. With native aprotinin a moderate inhibition was observed. The inhibition was strongly increased by analogues KFN 396 and KFN 399 containing Ala in position 17 (FIG. 5A).

A further increase of the inhibition was obtained with Arg in position 15 (KFN 772); and the strongest inhibition was observed with the analogue (KFN 773) with substitution of both position 17 (Ala) and position 15 (Arg) (FIG. 5B).

The analogues were also tested for inhibition of the amidolytic activity of the serine proteases: bovine factor Xa, human factor IIa, human recombinant factor VIIa and human recombinant protein Ca. The experiments were performed essentially as described for plasma kallikrein only appropriate substrates were used. Finally the analogues were analysed for an effect on the coagulation factors of human plasma by means of two clotting tests. These tests, the prothrombin time (PTT) and the activated thromboplastin time (APTT) were performed with General Diagnostics® reagents from Organon (Durham, N.C.) according to the directions given by the manufacturer. The results of the inhibition experiments are summarized in Table 4 which describes the inhibition profile of the four aprotinin analogues. KFN 773 is characterized by an extraordinaryly strong inhibition of human plasma kallikrein, which is ten fold stronger than that of the Arg 15 analogue (KFN 772). A reverse effect is observed with activated protein C. In this case the relatively strong inhibition obtained by substitution of Lys 15 to Arg is weakened by further substitution of Arg 17 to Ala.

TABLE 4

| | Inhibition profile of aprotinin analogues | | | | | | |
|---|---|---|---|---|---|---|---|
| | $K_i^*$ (nM); Amidolytic activity of serin proteases § | | | | | Clot assays | |
| Product | Plasma kallikrein | FIIa | FVIIa | FXa | Prot. Ca | PTT | APTT |
| Native Aprotinin | 180 | — | — | — | 400 | — | — |
| KFN 396 | 12 | — | — | — | — | — | — |
| KFN 399 | 12 | | | | | | |
| KFN 772 | 1 | — | — | 1800 | 10 | — | + |
| KFN 773 | 0.1 | — | — | 150 | 100 | — | + |

— No inhibition at 1.0 μM aprotinin analogue
+ Prolonged clotting time at 1.0 μM aprotinin analogue
*)Inhibition constants estimated according to the graphical Dixon method (M. Dixon, Biochem. J. 129 (1972)197–202)
§ Substrates: Plasma kallikrein: S2302; FIIa: S2238; FVIIa: Substrate FXa-1: Substrate FXa-1; Prot. Ca: S2366.

We claim:

1. An aprotinin analogue having an inhibitory effect against serine protease of the following formula:

$X_1$-Asp-Phe-Cys-Leu-Glu-Pro-Pro-Tyr-Thr-$X_2$-$X_3$-$X_4$-$X_5$-$X_6$-$X_7$-$X_8$-$X_9$-Arg-Tyr-Phe-Tyr-Asn-Ala-Lys-Ala-Gly-Leu-Cys-Gln-Thr-Phe-Val-Tyr-Gly-Gly-$X_{10}$-Arg-Ala-$X_{11}$-$X_{12}$-Asn-Asn-Phe-Lys-Ser-Ala-Glu-Asp-Cys-Met-Arg-Thr-Cys-Gly-Gly-Ala (SEQ ID NO: 2)

wherein
$X_1$ is Arg-Pro,Pro or hydrogen;
$X_2$ is Gly;
$X_3$ is Pro;
$X_4$ and $X_{10}$ are both Cys;
$X_5$ is Lys or Arg
$X_6$ is Ala or Gly;

2. The aprotinin analogue having the following sequence:

Arg-Pro-Asp-Phe-Cys-Leu-Glu-Pro-Pro-Tyr-Thr-Gly-Pro-Cys-Lys-Ala-Ala-Ile-Glu-Arg-Tyr-Phe-Tyr-Asn-Ala-Lys-Ala-Gly-Leu-Cys-Gln-Thr-Phe-Val-Tyr-Gly-Gly-Cys-Arg-Ala-Lys-Arg-Asn-Asn-Phe-Lys-Ser-Ala-Glu-Asp-Cys-Met-Arg-Thr-Cys-Gly-Gly-Ala (SEQ ID NO: 22).

3. The aprotinin analogue having the following sequence:

Arg-Pro-Asp-Phe-Cys-Leu-Glu-Pro-Pro-Tyr-Thr-Gly-Pro-Cys-Lys-Ala-Ala-Ile-Glu-Arg-Tyr-Phe-Tyr-Asn-Ala-Lys-Ala-Gly-Leu-Cys-Gln-Thr-Phe-Val-Tyr-Gly-Gly-Cys-Arg-Ala-Lys-Ser-Asn-Asn-Phe-Lys-Ser-Ala-Glu-Asp-Cys-Met-Arg-Thr-Cys-Gly-Gly-Ala (SEQ ID NO: 24).

4. The aprotinin analogue having the following sequence:

Arg-Pro-Asp-Phe-Cys-Leu-Glu-Pro-Pro-Tyr-Thr-Gly-Pro-Cys-Lys-Ala-Ala-Ile-Ile-Arg-Tyr-Phe-

Tyr-Asn-Ala-Lys-Ala-Gly-Leu-Cys-Gln-Thr-Phe-
Val-Tyr-Gly-Gly-Cys-Arg-Ala-Lys-Arg-Asn-
Asn-Phe-Lys-Ser-Ala-Glu-Asp-Cys-Met-Arg-Thr-
Cys-Gly-Gly-Ala (SEQ ID NO: 26).

5. The aprotinin analogue having the following sequence:

Arg-Pro-Asp-Phe-Cys-Leu-Glu-Pro-Pro-Tyr-Thr-
Gly-Pro-Cys-Lys-Ala-Ala-Ile-Ile-Arg-Tyr-Phe-
Tyr-Asn-Ala-Lys-Ala-Gly-Leu-Cys-Gln-Thr-Phe-
Val-Tyr-Gly-Gly-Cys-Arg-Ala-Lys-Ser-Asn-Asn-
Phe-Lys-Ser-Ala-Glu-Asp-Cys-Met-Arg-Thr-Cys-
Gly-Gly-Ala (SEQ ID NO: 29).

6. The aprotinin analogue having the following sequence:

Arg-Pro-Asp-Phe-Cys-Leu-Glu-Pro-Pro-Tyr-Thr-
Gly-Pro-Cys-Arg-Ala-Ala-Ile-Ile-Arg-Tyr-Phe-
Tyr-Asn-Ala-Lys-Ala-Gly-Leu-Cys-Gln-Thr-Phe-
Val-Tyr-Gly-Gly-Cys-Arg-Ala-Lys-Ser-Asn-Asn-
Phe-Lys-Ser-Ala-Glu-Asp-Cys-Met-Arg-Thr-Cys-
Gly-Gly-Ala (SEQ ID NO: 31).

* * * * *

UNITED STATES PATENT AND TRADEMARK OFFICE
CERTIFICATE OF CORRECTION

PATENT NO. : 5,373,090
DATED : December 13, 1994
INVENTOR(S) : Norris et al.

It is certified that error appears in the above-indentified patent and that said Letters Patent is hereby corrected as shown below:

Column 31, line 66
    claim 1:    after "$X_6$ is Ala or Gly", insert

-- $X_8$ is Ile;

$X_9$ is Glu or Ile;

$X_{11}$ is Lys or Arg;

$X_{12}$ is Lys, Arg or Ser; and $X_7$ is Ala or Gly. --

Signed and Sealed this

Twenty-eighth Day of November 1995

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
( A ) LENGTH: 58 amino acids
( B ) TYPE: amino acid
( D ) TOPOLOGY: linear ( i i ) MOLECULE TYPE: protein ( v i ) ORIGINAL SOURCE:
( A ) ORGANISM: bovine ( x i ) SEQUENCE DESCRIPTION: SEQ ID NO:1:

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
        20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
        50                  55

( 2 ) INFORMATION FOR SEQ ID NO:2:

( i ) SEQUENCE CHARACTERISTICS:
( A ) LENGTH: 57 amino acids
( B ) TYPE: amino acid
( D ) TOPOLOGY: linear ( i i ) MOLECULE TYPE: protein ( v i ) ORIGINAL SOURCE:
( A ) ORGANISM: synthetic ( x i ) SEQUENCE DESCRIPTION: SEQ ID NO:2:

Xaa Asp Phe Cys Leu Glu Pro Pro Tyr Thr Xaa Xaa Xaa Xaa Xaa Xaa
1               5                   10                  15

Xaa Xaa Arg Tyr Phe Tyr Asn Ala Lys Ala Gly Leu Cys Gln Thr Phe
        20                  25                  30

Val Tyr Gly Gly Xaa Arg Ala Xaa Xaa Asn Asn Phe Lys Ser Ala Glu
        35                  40                  45

Asp Cys Met Arg Thr Cys Gly Gly Ala
        50                  55

( 2 ) INFORMATION FOR SEQ ID NO:3:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO:3:

```
Xaa Asp Phe Cys Leu Glu Pro Pro Tyr Thr Gly Pro Cys Xaa Xaa Xaa
 1               5                   10                  15

Xaa Xaa Arg Tyr Phe Tyr Asn Ala Lys Ala Gly Leu Cys Gln Thr Phe
             20                  25                  30

Val Tyr Gly Gly Cys Arg Ala Xaa Xaa Asn Asn Phe Lys Ser Ala Glu
         35                  40                  45

Asp Cys Met Arg Thr Cys Gly Gly Ala
 50                      55
```

( 2 ) INFORMATION FOR SEQ ID NO:4:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO:4:

```
Xaa Asp Phe Cys Leu Glu Pro Pro Tyr Thr Gly Pro Cys Lys Xaa Xaa
 1               5                   10                  15

Xaa Xaa Arg Tyr Phe Tyr Asn Ala Lys Ala Gly Leu Cys Gln Thr Phe
             20                  25                  30

Val Tyr Gly Gly Cys Arg Ala Xaa Xaa Asn Asn Phe Lys Ser Ala Glu
         35                  40                  45

Asp Cys Met Arg Thr Cys Gly Gly Ala
 50                      55
```

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: synthetic ( x i ) SEQUENCE DESCRIPTION: SEQ ID NO:5:

AAAGAGATTT CTGTTTGGAA CCTCCATACA CTGGTCC        37

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (  i  i  ) MOLECULE TYPE: DNA (  v  i  ) ORIGINAL SOURCE:
   ( A ) ORGANISM: synthetic (  x  i  ) SEQUENCE DESCRIPTION: SEQ ID NO:6:

TTACATGGAC CAGTGTATGG AGGTTCCAAA CAGAAACT    38

( 2 ) INFORMATION FOR SEQ ID NO:7:

(  i  ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear (  i  i  ) MOLECULE TYPE: DNA (  v  i  ) ORIGINAL SOURCE:
      ( A ) ORGANISM: synthetic (  x  i  ) SEQUENCE DESCRIPTION: SEQ ID NO:7:

ATGTAAAGCT AGAATCATCA GATACTTCTA CAACG    35

( 2 ) INFORMATION FOR SEQ ID NO:8:

(  i  ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear (  i  i  ) MOLECULE TYPE: DNA (  v  i  ) ORIGINAL SOURCE:
      ( A ) ORGANISM: synthetic (  x  i  ) SEQUENCE DESCRIPTION: SEQ ID NO:8:

CTTGGCGTTG TAGAAGTATC TGATGATTCT AGCT    34

( 2 ) INFORMATION FOR SEQ ID NO:9:

(  i  ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear (  i  i  ) MOLECULE TYPE: DNA (  v  i  ) ORIGINAL SOURCE:
      ( A ) ORGANISM: synthetic (  x  i  ) SEQUENCE DESCRIPTION: SEQ ID NO:9:

CCAAGGCTGG TTTGTGTCAA ACTTTCGTTT ACGGTGGCT    39

( 2 ) INFORMATION FOR SEQ ID NO:10:

(  i  ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear (  i  i  ) MOLECULE TYPE: DNA (  v  i  ) ORIGINAL SOURCE:
      ( A ) ORGANISM: synthetic (  x  i  ) SEQUENCE DESCRIPTION: SEQ ID NO:10:

CTCTGCAGCC ACCGTAAACG AAAGTTTGAC ACAAACCAGC    40

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: synthetic ( x i ) SEQUENCE DESCRIPTION: SEQ ID NO:11:

GCAGAGCTAA GTCCAACAAC TTCAAGT        27

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: synthetic ( x i ) SEQUENCE DESCRIPTION: SEQ ID NO:12:

AGCAGACTTG AAGTTGTTGG ACTTAG        26

( 2 ) INFORMATION FOR SEQ ID NO:13:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: synthetic ( x i ) SEQUENCE DESCRIPTION: SEQ ID NO:13:

CTGCTGAAGA CTGCATGAGA ACTTGTGGTG GTGCCTAAT        39

( 2 ) INFORMATION FOR SEQ ID NO:14:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: synthetic ( x i ) SEQUENCE DESCRIPTION: SEQ ID NO:14:

CTAGATTAGG CACCACCACA AGTTCTCATG CAGTCTTC        38

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (v i) ORIGINAL SOURCE:
    (A) ORGANISM: synthetic (x i) SEQUENCE DESCRIPTION: SEQ ID NO:15:

CTGGTCCATG TAAAGCTGCT ATCATCAGAT ACTTCTACAA CGC    43

(2) INFORMATION FOR SEQ ID NO:16:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (v i) ORIGINAL SOURCE:
        (A) ORGANISM: synthetic (x i) SEQUENCE DESCRIPTION: SEQ ID NO:16:

CTTGGCGTTG TAGAAGTATC TGATGATAGC AGCTTTACAT GGACCAGTGT    50

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (i i) MOLECULE TYPE: protein (v i) ORIGINAL SOURCE:
        (A) ORGANISM: synthetic (x i) SEQUENCE DESCRIPTION: SEQ ID NO:17:

Thr Gly Pro Cys Lys Ala Ala Ile Ile Arg Tyr Phe Tyr Asn Ala
 1           5                   10                  15

(2) INFORMATION FOR SEQ ID NO:18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (v i) ORIGINAL SOURCE:
        (A) ORGANISM: synthetic (x i) SEQUENCE DESCRIPTION: SEQ ID NO:18:

CTGGTCCATG TAAAGCTGCT ATCGAAAGAT ACTTCTACAA CGC    43

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (v i) ORIGINAL SOURCE:
        (A) ORGANISM: synthetic (x i) SEQUENCE DESCRIPTION: SEQ ID NO:19:

CTTGGCGTTG TAGAAGTATC TTTCGATAGC AGCTTTACAT GGACCAGTGT    50

(2) INFORMATION FOR SEQ ID NO:20:

( i ) SEQUENCE CHARACTERISTICS:
   ( A ) LENGTH: 43 base pairs
   ( B ) TYPE: nucleic acid
   ( C ) STRANDEDNESS: single
   ( D ) TOPOLOGY: linear ( i i ) MOLECULE TYPE: DNA ( v i ) ORIGINAL SOURCE:
   ( A ) ORGANISM: synthetic ( x i ) SEQUENCE DESCRIPTION: SEQ ID NO:20:

CTGGTCCATG TAGAGCTGCT ATCATCAGAT ACTTCTACAA CGC          43

( 2 ) INFORMATION FOR SEQ ID NO:21:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA ( v i ) ORIGINAL SOURCE:
      ( A ) ORGANISM: synthetic ( x i ) SEQUENCE DESCRIPTION: SEQ ID NO:21:

CTTGGCGTTG TAGAAGTATC TGATGATAGC AGCTCTACAT GGACCAGTGT          50

( 2 ) INFORMATION FOR SEQ ID NO:22:

( i ) SEQUENCE CHARACTERISTICS:
      ( A ) LENGTH: 58 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: synthetic ( x i ) SEQUENCE DESCRIPTION: SEQ ID NO:22:

```
Arg Pro Asp Phe Cys Leu Glu Pro Pro Tyr Thr Gly Pro Cys Lys Ala
1               5                   10                  15

Ala Ile Glu Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
            35              40                  45

Glu Asp Cys Met Arg Thr Cys Gly Gly Ala
        50              55
```

( 2 ) INFORMATION FOR SEQ ID NO:23:

( i ) SEQUENCE CHARACTERISTICS:
      ( A ) LENGTH: 56 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: synthetic ( x i ) SEQUENCE DESCRIPTION: SEQ ID NO:23:

```
Asp Phe Cys Leu Glu Pro Pro Tyr Thr Gly Pro Cys Lys Ala Ala Ile
1               5                   10                  15

Glu Arg Tyr Phe Tyr Asn Ala Lys Ala Gly Leu Cys Gln Thr Phe Val
            20                  25                  30

Tyr Gly Gly Cys Arg Ala Lys Arg Asn Asn Phe Lys Ser Ala Glu Asp
```

Cys Met Arg Thr Cys Gly Gly Ala
50                      55

( 2 ) INFORMATION FOR SEQ ID NO:24:

( i ) SEQUENCE CHARACTERISTICS:
       ( A ) LENGTH: 58 amino acids
       ( B ) TYPE: amino acid
       ( D ) TOPOLOGY: linear ( i i ) MOLECULE TYPE: protein ( v i ) ORIGINAL SOURCE:
       ( A ) ORGANISM: synthetic ( x i ) SEQUENCE DESCRIPTION: SEQ ID NO:24:

Arg Pro Asp Phe Cys Leu Glu Pro Pro Tyr Thr Gly Pro Cys Lys Ala
1               5                   10                  15

Ala Ile Glu Arg Tyr Phe Tyr Asn Ala Lys Ala Gly Leu Cys Gln Thr
            20                  25                  30

Phe Val Tyr Gly Gly Cys Arg Ala Lys Ser Asn Asn Phe Lys Ser Ala
        35                  40                  45

Glu Asp Cys Met Arg Thr Cys Gly Gly Ala
50                      55

( 2 ) INFORMATION FOR SEQ ID NO:25:

( i ) SEQUENCE CHARACTERISTICS:
       ( A ) LENGTH: 56 amino acids
       ( B ) TYPE: amino acid
       ( D ) TOPOLOGY: linear ( i i ) MOLECULE TYPE: protein ( v i ) ORIGINAL SOURCE:
       ( A ) ORGANISM: synthetic ( x i ) SEQUENCE DESCRIPTION: SEQ ID NO:25:

Asp Phe Cys Leu Glu Pro Pro Tyr Thr Gly Pro Cys Lys Ala Ala Ile
1               5                   10                  15

Glu Arg Tyr Phe Tyr Asn Ala Lys Ala Gly Leu Cys Gln Thr Phe Val
            20                  25                  30

Tyr Gly Gly Cys Arg Ala Lys Ser Asn Asn Phe Lys Ser Ala Glu Asp
        35                  40                  45

Cys Met Arg Thr Cys Gly Gly Ala
50                      55

( 2 ) INFORMATION FOR SEQ ID NO:26:

( i ) SEQUENCE CHARACTERISTICS:
       ( A ) LENGTH: 58 amino acids
       ( B ) TYPE: amino acid
       ( D ) TOPOLOGY: linear ( i i ) MOLECULE TYPE: protein ( v i ) ORIGINAL SOURCE:
       ( A ) ORGANISM: synthetic ( x i ) SEQUENCE DESCRIPTION: SEQ ID NO:26:

Arg Pro Asp Phe Cys Leu Glu Pro Pro Tyr Thr Gly Pro Cys Lys Ala
1               5                   10                  15

Ala Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

```
            Glu  Asp  Cys  Met  Arg  Thr  Cys  Gly  Gly  Ala
                  50                  55
```

( 2 ) INFORMATION FOR SEQ ID NO:27:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO:27:

```
Asp  Phe  Cys  Leu  Glu  Pro  Pro  Tyr  Thr  Gly  Pro  Cys  Lys  Ala  Ala  Ile
 1                  5                            10                        15

Ile  Arg  Tyr  Phe  Tyr  Asn  Ala  Lys  Ala  Gly  Leu  Cys  Gln  Thr  Phe  Val
               20                       25                        30

Tyr  Gly  Gly  Cys  Arg  Ala  Lys  Arg  Asn  Asn  Phe  Lys  Ser  Ala  Glu  Asp
          35                       40                       45

Cys  Met  Arg  Thr  Cys  Gly  Gly  Ala
      50                  55
```

( 2 ) INFORMATION FOR SEQ ID NO:28:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO:28:

```
Asp  Phe  Cys  Leu  Glu  Pro  Pro  Tyr  Thr  Gly  Pro  Cys  Lys  Ala  Ala  Ile
 1                  5                            10                        15

Ile  Arg  Tyr  Phe  Tyr  Asn  Ala  Lys  Ala  Gly  Leu  Cys  Gln  Thr  Phe  Val
               20                       25                        30

Tyr  Gly  Gly  Cys  Arg  Ala  Lys  Ser  Asn  Asn  Phe  Lys  Ser  Ala  Glu  Asp
          35                       40                       45

Cys  Met  Arg  Thr  Cys  Gly  Gly  Ala
      50                  55
```

( 2 ) INFORMATION FOR SEQ ID NO:29:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO:29:

```
Arg  Pro  Asp  Phe  Cys  Leu  Glu  Pro  Pro  Tyr  Thr  Gly  Pro  Cys  Lys  Ala
 1                  5                            10                        15

Ala  Ile  Ile  Arg  Tyr  Phe  Tyr  Asn  Ala  Lys  Ala  Gly  Leu  Cys  Gln  Thr
               20                       25                        30

Phe  Val  Tyr  Gly  Gly  Cys  Arg  Ala  Lys  Ser  Asn  Asn  Phe  Lys  Ser  Ala
          35                       40                       45
```

```
       Glu  Asp  Cys  Met  Arg  Thr  Cys  Gly  Gly  Ala
            50                  55
```

( 2 ) INFORMATION FOR SEQ ID NO:30:

( i ) SEQUENCE CHARACTERISTICS:
      ( A ) LENGTH: 56 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: synthetic ( x i ) SEQUENCE DESCRIPTION: SEQ ID NO:30:

```
Asp  Phe  Cys  Leu  Glu  Pro  Pro  Tyr  Thr  Gly  Pro  Cys  Arg  Ala  Ala  Ile
 1             5                      10                       15

Ile  Arg  Tyr  Phe  Tyr  Asn  Ala  Lys  Ala  Gly  Leu  Cys  Gln  Thr  Phe  Val
               20                       25                       30

Tyr  Gly  Gly  Cys  Arg  Ala  Lys  Ser  Asn  Asn  Phe  Lys  Ser  Ala  Glu  Asp
          35                       40                       45

Cys  Met  Arg  Thr  Cys  Gly  Gly  Ala
     50                  55
```

( 2 ) INFORMATION FOR SEQ ID NO:31:

( i ) SEQUENCE CHARACTERISTICS:
      ( A ) LENGTH: 58 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: synthetic ( x i ) SEQUENCE DESCRIPTION: SEQ ID NO:31:

```
Arg  Pro  Asp  Phe  Cys  Leu  Glu  Pro  Pro  Tyr  Thr  Gly  Pro  Cys  Arg  Ala
 1             5                      10                       15

Ala  Ile  Ile  Arg  Tyr  Phe  Tyr  Asn  Ala  Lys  Ala  Gly  Leu  Cys  Gln  Thr
               20                       25                       30

Phe  Val  Tyr  Gly  Gly  Cys  Arg  Ala  Lys  Ser  Asn  Asn  Phe  Lys  Ser  Ala
          35                       40                       45

Glu  Asp  Cys  Met  Arg  Thr  Cys  Gly  Gly  Ala
     50                  55
```

( 2 ) INFORMATION FOR SEQ ID NO:32:

( i ) SEQUENCE CHARACTERISTICS:
      ( A ) LENGTH: 177 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Synthetic ( i x ) FEATURE:
      ( A ) NAME/KEY: CDS
      ( B ) LOCATION: 6..173

( x i ) SEQUENCE DESCRIPTION: SEQ ID NO:32:

```
AAAGA GAT TTC TGT TTG GAA CCT CCA TAC ACT GGT CCA TGT AAA GCT           47
      Asp Phe Cys Leu Glu Pro Pro Tyr Thr Gly Pro Cys Lys Ala
       1           5                      10
```

| | | | | | | | | | | | | | | |
|---|---|---|---|---|---|---|---|---|---|---|---|---|---|---|
| AGA | ATC | ATC | AGA | TAC | TTC | TAC | AAC | GCC | AAG | GCT | GGT | TTG | TGT | CAA | ACT | 95
| Arg | Ile | Ile | Arg | Tyr | Phe | Tyr | Asn | Ala | Lys | Ala | Gly | Leu | Cys | Gln | Thr |
| 15 | | | | 20 | | | | | 25 | | | | | 30 | |

| | | | | | | | | | | | | | | |
|---|---|---|---|---|---|---|---|---|---|---|---|---|---|---|
| TTC | GTT | TAC | GGT | GGC | TGC | AGA | GCT | AAG | TCC | AAC | AAC | TTC | AAG | TCT | GCT | 143
| Phe | Val | Tyr | Gly | Gly | Cys | Arg | Ala | Lys | Ser | Asn | Asn | Phe | Lys | Ser | Ala |
| | | | | 35 | | | | | 40 | | | | | 45 | |

| | | | | | | | | |
|---|---|---|---|---|---|---|---|---|
| GAA | GAC | TGC | ATG | AGA | ACT | TGT | GGT | GGT | GCC | TAAT | 177
| Glu | Asp | Cys | Met | Arg | Thr | Cys | Gly | Gly | Ala |
| | | | 50 | | | | | 55 | |

(2) INFORMATION FOR SEQ ID NO:33:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:33:

Asp Phe Cys Leu Glu Pro Pro Tyr Thr Gly Pro Cys Lys Ala Arg Ile
1               5                   10                  15

Ile Arg Tyr Phe Tyr Asn Ala Lys Ala Gly Leu Cys Gln Thr Phe Val
            20                  25                  30

Tyr Gly Gly Cys Arg Ala Lys Ser Asn Asn Phe Lys Ser Ala Glu Asp
        35                  40                  45

Cys Met Arg Thr Cys Gly Gly Ala
        50              55

(2) INFORMATION FOR SEQ ID NO:34:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Synthetic (xi) SEQUENCE DESCRIPTION: SEQ ID NO:34:

CTAGATTAGG CACCACCACA AGTTCTCATG CAGTCTTCAG CAGACTTGAA GTTGTTGGAC      60

TTAGCTCTGC AGCCACCGTA AACGAAAGTT TGACACAAAC CAGCCTTGGC GTTGTAGAAG     120

TATCTGATGA TTCTAGCTTT ACATGGACCA GTGTATGGAG GTTCCAAACA GAAATC         176